United States Patent [19]

Garlick et al.

[11] Patent Number: 4,737,000
[45] Date of Patent: * Apr. 12, 1988

[54] APPARATUS FOR DIVERTING ELECTROMAGNETIC RADIATION FROM SENSITIVE OPTICAL APPARATUS

[75] Inventors: George F. J. Garlick, Los Angeles; David R. Lillington, Van Nuys; Joseph A. Minahan, Simi Valley, all of Calif.

[73] Assignee: Hughes Aircraft Company, Los Angeles, Calif.

[*] Notice: The portion of the term of this patent subsequent to Jan. 12, 2005 has been disclaimed.

[21] Appl. No.: 883,690

[22] Filed: Jul. 9, 1986

[51] Int. Cl.$^4$ ................................. G02F 1/00
[52] U.S. Cl. ........................... 350/1.7; 350/363
[58] Field of Search ................. 350/1.1, 1.7, 363

[56] References Cited

U.S. PATENT DOCUMENTS

| | | | |
|---|---|---|---|
| 3,213,752 | 10/1965 | Ruderman | 88/61 |
| 3,414,838 | 12/1968 | De Ment | 331/94.5 |
| 3,893,129 | 7/1975 | Endo et al. | 346/77 E |
| 4,002,403 | 1/1977 | Mallozzi et al. | 350/160 R |

Primary Examiner—Bruce Y. Arnold
Attorney, Agent, or Firm—Ronald L. Taylor; A. W. Karambelas

[57] ABSTRACT

Apparatus is disclosed for protecting delicate sensor optics from the damaging effects of unwanted powerful laser radiation. A thin-film reflective pellicle 14 is placed in the light path of a sensor telescope. Incident light 10 is focused by some combination of optical elements 12 onto the reflective surface 28 of the laser hazard protector 14. The reflected light 10 is then imaged by further optics 16 onto a detector array 18. Should a signal too strong for the detector enter the sensor aperture with the incident light 10, the focused power at the surface of the pellicle 28 will ablate the carbon and metallic film, burning a hole in the pellicle, and the high-power light 11 will be deflected from the detector array and be absorbed instead by the beam dump 20. A power meter within the beam dump determines when the laser threat has stopped and signals the turning mechanisms 15a and 15b to turn the pellicle reflector to a fresh position at which point normal sensor operations may resume. The reflective film for the laser hazard protector has a carbon supporting film placed after the reflective coating. The reflective coating has a uniform broadband absorption to laser light and can protect a sensor from a variety of potential threats. The present invention provides a sensor protection system with an extremely short response time, widband protection, and an unmatched margin of safety.

8 Claims, 4 Drawing Sheets

APPARATUS FOR DIVERTING ELECTROMAGNETIC RADIATION FROM SENSITIVE OPTICAL APPARATUS

BACKGROUND OF THE INVENTION

The present patent application is related to a patent application entitled "Electromagnetic Energy Diversion Device Responsive to the Power Density of the Energy" (formerly "Pellicle Laser Power Limiter") by David B. Cohn and Lorna C. Finman, filed on July 9, 1986 and assigned to Hughes Aircraft Company.

1. Field of the Invention

The present invention pertains to visible and infrared detectors and sensor systems. The specific focus of the invention is the protection of sensitive sensor components from the damaging effects of radiation from high-power laser sources.

2. Background Information

The field of optical engineering divides into two principal areas of practice. On one hand, light (that is, ultraviolet (UV), infrared (IR), and visible electromagnetic radiation) is generated, manipulated, and utilized for a myriad of imaging, diagnostic, and metrological purposes. On the other hand, the created and utilized light must be sensed by some arrangement of detectors for its full utility to be realized. When optics was still young as a discipline, the principal sensing system was either the human eye or a photographic emulsion. But as the field of optical science has burgeoned in recent years, ever more sensitive and accurate detectors have been required.

The techniques of semiconductor fabrication have produced extraordinarily accurate sensing devices. Focal plane arrays rely on photoconductive effects in semiconductor junctions to register incidence of light upon their surface. When combined in optical systems incorporating light-gathering apparatus, such as in a camera, focal plane arrays produce electrical signals which very accurately duplicate the image or light wavefront being detected. The resulting signals can then be operated upon by electrical signal processing equipment and be available for certain desired effects. The detection network described above forms the basis of television signal generation. Light detection systems are also central to the world's vast network of satellite cameras and mappers. Since focal plane arrays may be designed for specific wavelengths of light, a satellite mapper can detect the visible light from terrestrial weather, the infrared patterns of land and vegetation, or ultraviolet disturbances on the sun.

Laboratory uses for detectors are also manifold. The accuracy and flexibility afforded by optical instrumentation ensures the importance of reliable, sensitive detectors for industry and science.

The greatest strength of the new generation of detectors, i.e., their ability to accurately record light images at very low intensity, proves to be their greatest weakness. Inadvertent pulses of high-intensity light, focused upon these focal plane arrays by powerful optical elements, can temporarily saturate or permanently damage their thin and fragile semiconductor surfaces. The omnipresence of the laser in laboratory settings greatly increases the risk of accidental destruction of expensive precision detection equipment. In addition, military sensors (for instance, IR sensors used to see at night or in smoke-filled environments) are particularly vulnerable to unfriendly jamming and damage from laser sources. All detectors used to monitor low-level light intensities require some form of protection against careless or willful destruction.

Only recently has much effort been expended to create the needed protection methods for sensitive detectors. A variety of means for protection against high-intensity laser radiation have been proposed and investigated, some more esoteric than others. The simplest and most obvious protection device is a mechanical shutter. When the focal plane array detects some unacceptable rise in light intensity, a shutter closes over the aperture. The difficulty with this method is the intrinsically long risetime for moving the mass of the shutter into place. The laser radiation may damage the substrate within nanoseconds; by the time the shutter has closed off all further radiation, the sensor has been destroyed.

In order to improve the risetimes of the protection methods, various optical phenomena have been exploited to prevent harmful high-power light from striking the detector. For instance, certain gases under high pressure will strongly absorb radiation at a particular wavelength while transmitting all others. However, this method also has severe disadvantages. First, the high pressures involved can be dangerous, and, second, the method does not provide broadband protection from a variety of potential threats. Even when the gases do absorb hazardous laser light, the absorption is never total and a strong enough signal will eventually overpower this method of protection.

Similarly, absorbing optical coatings composed of dielectric and metallic films have been tried to absorb light of particular wavelengths. Presumably, all feasible laser threats would be catalogued, the most likely selected to protect against, and absorbing filters would be designed and constructed to eliminate only those wavelengths. Again, such band-stop filter techniques never totally prevent a strong light signal from reaching the detector surface. Moreover, the protected bands prevent desired radiation at those wavelengths from entering the detector, sharply reducing the signal-to-noise ratio for the sensor.

Several nonlinear optical effects have been exploited in attempting to protect sensor systems. Nonlinear defocusing in liquid crystal media, which causes divergence of high-power laser beams, can provide broadband protection against laser threats. However, it too has a rather long risetime for its protective effects to occur. The various techniques for nonlinear phase conjugation have also been proposed to defend detector arrays. In these approaches, a nonlinear medium pumped by sensor-based laser sources can very efficiently reflect backwards a potentially damaging high-power laser beam. Unfortunately, phase conjugation methods are extremely sensitive to wavelength, requiring that a threat be known very accurately in advance. In addition, as with the nonlinear defocusing effect, enormous power densities are required before this technique will work. Most nonlinear effects, while useful in other areas of optical science, are inadequate for wideband protection of delicate sensor systems.

Instead of preventing hazardous radiation from reaching the focal plane, attempts have been made to "harden" the detector array itself. In U.S. Pat. No. 4,117,329, Kruer et al. describe a technique for constructing detectors which are thermally connected to large heat sinks. The resulting configuration allows absorbed heat radiation to be efficiently carried away from the photoconductive material at the detector surface.

A truly practical and reliable means for protecting detector arrays from the damaging effects of stray high-power laser radiation without effecting great alterations to conventional sensor designs would constitute a major advance in the optical engineering field. Such an invention would satisfy a long-felt need experienced by the optical science community for over two decades. Producers of sensors and detectors could employ such an innovative device to conveniently defend costly and sensitive sensor components from all possible kinds of laser-induced damage. Such an invention would ideally be suited to operate in cooperation with a wide variety of sensing systems and detector arrays and would perform consistently and reliably over a wide range of operating conditions in various system applications.

SUMMARY OF THE INVENTION

The aim of the present invention is to help accomplish the major technological advancement described above. The laser hazard protector provides a simple, flexible, and efficient means for protecting sensor apparatus from potentially damaging laser radiation. The device can be implemented by opto-mechanical engineers in a variety of detector settings, to achieve a level of equipment safety previously thought to be unattainable.

The laser hazard protector comprises a thin-film plastic or carbon substrate and a reflective coating. The coated film stretches across a supporting ring which maintains the flatness of the pellicle reflector. An arrangement of shafts, bearings, and motors, akin to the capstans in a tape recorder, support the pellicle ring and turn it when necessary. The device functions exactly as another reflective surface in the optical train of the particular sensor being protected. Light entering the sensor is focused by lenses or mirrors before striking the pellicle's reflective surface. Therefore, all the light now forms a small spot on the pellicle coating. Under normal operation this does not impair the operation of the associated optics: the light reflects off the pellicle, is imaged by further optical devices, and is detected by the focal plane array. However, if a large pulse of laser light enters the detector aperture, focusing the laser energy will cause the power density to exceed the heat limits of the film being used for the pellicle membrane. The membrane will absorb the energy, will ablate or vaporize, and instead of reflecting from the pellicle mirror the laser energy will pass through the membrane reflector and be absorbed within a beam dump.

Once the laser threat has diminished, as determined by a power meter within the beam dump, the pellicle reflector spins around to a fresh position and normal sensor operation resumes. The protection afforded by the laser hazard protector does not impair the normal operations of the sensor package except during those periods when excessive laser radiation would cause damage to the detector. In addition, because the spot size of light incident upon the pellicle is variable, the protection threshold of the device can be tailored for different applications and for different laser energy threats.

It is, therefore, an object of the present invention to provide apparatus for protecting sensor systems from possible hazardous laser threats.

Another object of the invention is to provide a simple, low-cost method for protecting detector arrays.

Still another object of the invention is to provide an adjustable laser power limiter capable of being tailored for particular system and environmental requirements.

It is also an object of the invention to provide a recyclable laser power limiter which can defend against a succession of damaging laser pulses.

Yet another object of the invention is to furnish a sensor protection device with an extremely fast risetime, one that is able to protect against extremely short laser pulses.

Still another object of the invention is to provide a device capable of protecting other optics from laser power hazards at any particular wavelength.

An appreciation of other aims and objects of the present invention and a more complete and comprehensive understanding of this invention may be achieved by studying the following description of a preferred embodiment and by referring to the accompanying drawings.

BRIEF DESCRIPTION OF THE DRAWINGS

FIG. 3 reveals cross-sectional views of the reflective pellicle laser hazard protector.

DESCRIPTION OF A PREFERRED EMBODIMENT

Figure 1:
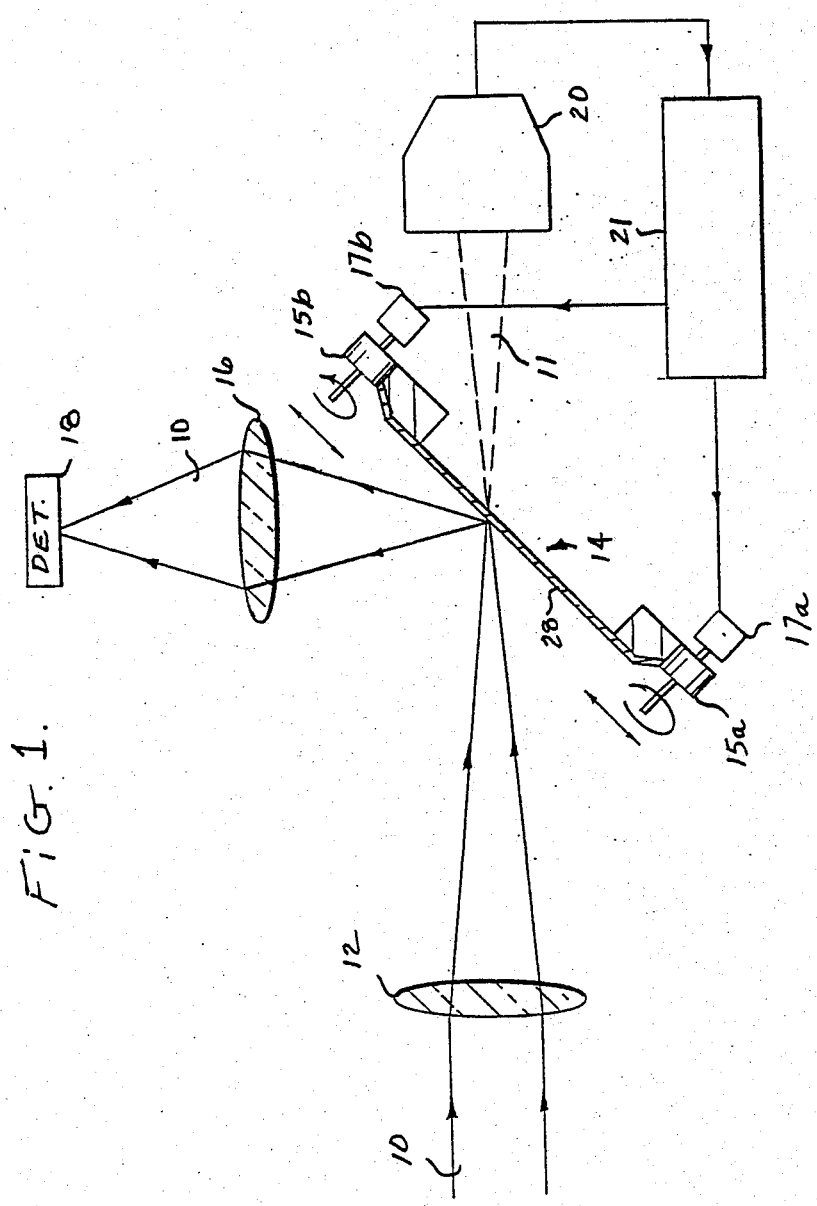
FIG. 1 is a schematic view of a generic sensor system composed of focusing elements, a detector array, and the laser hazard protector with its associated beam dump.

FIG. 1 depicts a protected sensor configuration employing a reflective laser hazard protector. As with any conventional radiation detector, incoming radiation 10 is focused through an objective 12 and imaging optics 16 onto a detector focal plane 18. However, to protect against damaging laser radiation, the present invention, a laser hazard protector 14, is inserted in the optical path. The objective element 12 first focuses incoming radiation upon the pellicle's reflective surface 28. This surface then reflects the radiation into an imaging element 16 (which alternatively might be a configuration of lenses) which focuses the radiation 10 upon the focal plane 18.

Because the objective 12 tightly focuses the incoming radiation 10 upon the pellicle surface 28, any large amount of radiant energy, such as from a powerful laser light source, would create an enormous power density at the focal point. The sharp rise in power flux upon the pellicle membrane will either ablate or melt the support substrate and the reflective coating, burning a hole in the pellicle and sending the radiation through the membrane to the rear side of the pellicle into a beam dump 20. A beam dump comprises a cavity in some absorbing medium, either a metal or composite plastic, which dissipates its heat by convection or by surrounding the cavity with a fluid cooling jacket. How much heat sinking is required depends upon the amount of energy that is expected to be deposited. The aperture to the cavity is small so that all light entering the beam dump will be absorbed before it has a chance to escape.

Within the beam dump, some type of power meter can be placed. The power meter can be a conventional copper-constantan thermocouple whose voltage varies as a function of temperature. The power meter will sense when the power has decreased to harmless levels in order to allow normal functioning of the detector 18 to proceed. Using a simple electrical feedback system 21, easily constructed by those skilled in the art, the power meter is connected to the turning mechanisms of the laser hazard protector.

One form for such a feedback system 21 is to have a human operator monitor a voltage meter attached to the thermocouple. When the voltage drops to normal operational levels, indicating that no more radiant energy is being dissipated by the beam dump 20, the operator can then manually turn the pellicle to a new position. Alternatively, using an electrical feedback system 21 as described above, when the radiation threat stops, capstans 15a,b operated by motors 17a,b (or any other suitable turning mechanisms mounted around the rim) spin the pellicle laser hazard protector 14 around to a fresh position where the pellicle membrane is undamaged and the imaging quality is good. At this point, the sensor device is once again fully operational. The rotation of the pellicle can be augmented by a translation, so that much of the pellicle surface may be used before the device requires replacing. These various motions are illustrated in FIG. 1 by the arrows near capstans 15a,b.

Figure 2:
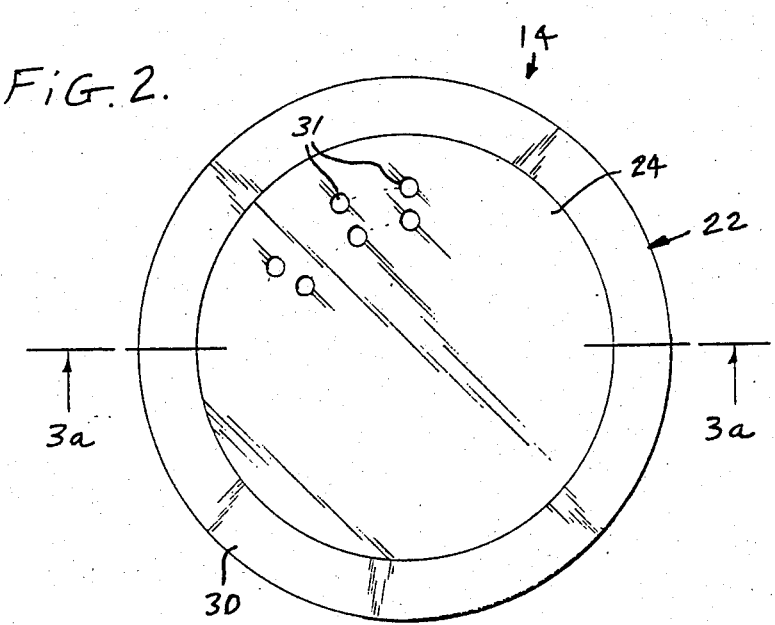
FIG. 2 is a top view of the pellicle reflector showing its support ring and several laser burn holes through the membrane surface.
Figure 3A:
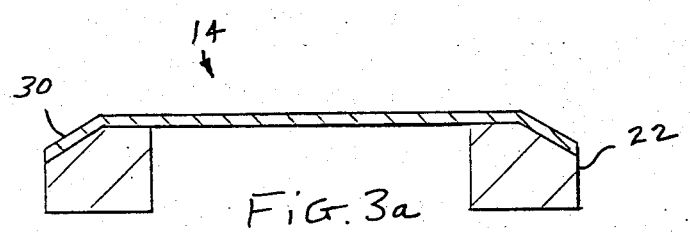
FIG. 3a shows the entire pellicle in cross-section.

FIGS. 2 and 3 show various views of the pellicle laser power limiter. FIG. 2 shows a top view with several burn holes 31 along arcs on the membrane 24 surface, while FIG. 3a presents a cross-sectional view of the pellicle. The pellicle can be composed of an optically-flat coated polymer membrane 24 stretched taut across a support ring 22. The membrane 24 is attached to the support ring 22 along the bevels 30 around the ring's outer edge. An adhesive epoxy may be used as a bonding medium for attaching the membrane to the support ring mounting apparatus. The membrane 24 can be produced by various replication methods known to those skilled in the art, among which are casting, spin-coating, or vapor-deposition upon an optically flat replication master. Such methods can achieve an optical flatness of one-tenth of a wavelength of light or better in the infrared spectrum. Therefore, the imaging quality of the membrane reflector (pellicle) will be quite adequate for most sensor and detector applications.

Alternatively, the substrate material can be a very thin carbon (or other organic substance) film which is placed behind the reflective coating and supports it mechanically. This film can be deposited by a variety of techniques in order to give strength and the proper optical flatness to the reflector layer.

Figure 3B:
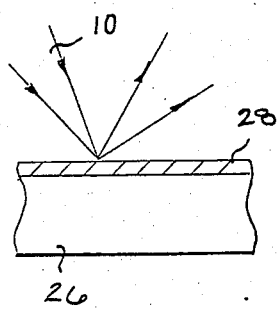
FIG. 3b shows a part of the membrane with reflective layer on top, facing the focused incident radiation.
Figure 3C:
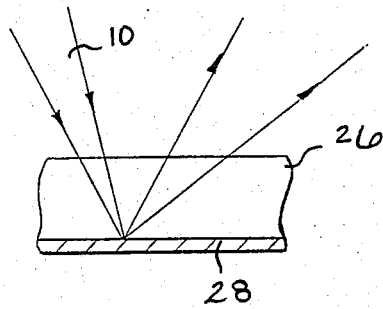
FIG. 3c shows a part of the membrane with the reflective layer on the bottom and the plastic substrate on top, facing the incident radiation.

FIGS. 3b and 3c illustrate two membrane coating configurations. FIG. 3b pertains to the present invention, FIG. 3c refers to a membrane configuration described in the related patent application Electromagnetic Energy Diversion Device Responsive to the Power Density of the Energy, previously cross referenced. In both these membrane cases, the incident radiation 10 is focused on the reflective layer 28 and is reflected from it. The first case, FIG. 3b, relies upon the reflective layer's inherent absorption to cause the damage to the membrane. For instance, if the reflective layer were a thin flash-deposition of aluminum, it will have an absorption of around 4 to 6% across the detector's operating spectrum. The backing substrate does not need to be transmissive and can be the described carbon film. Thinness of the film would be required to enable rapid absorption of heat energy and the quick subsequent destruction of the reflective film. Having the reflective layer absorb the harmful energy provides broadband protection from a variety of conceivable high-power radiation sources. Although the configuration shown in FIG. 3c allows specific absorption peaks in the plastic film to strongly absorb a given laser threat, this second approach has the concomitant disadvantage that radiation in the protected portion of the spectrum will also not be transmitted to the detector 18, resulting in a potential lowering of the signal-to-noise ratio for the detector. The present invention, by placing the reflective layer at the front of the pellicle as in FIG. 3b, has a uniform signal-to-noise characteristic across the sensor's operating spectrum.

An optimal system arrangement for the laser hazard protector can be obtained by varying several of its parameters. The size of the spot at the focus depends on the focal length and quality of the objective lens 12 and the distance to the laser hazard protector 14. For a given high-power threat, the focal spot size determines the power density that the system will achieve at the membrane's surface. Therefore, the sensitivity of the system to damage can be adjusted by changing the spot size.

Figure 4:
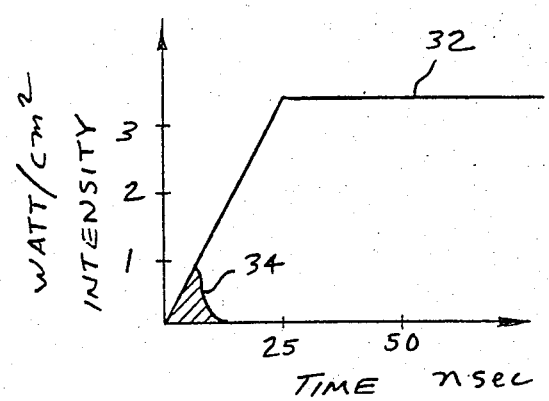
FIG. 4 is a graph of radiant intensity at the detector surface as a function of time for a continuous-wave laser threat. One line is a plot of intensity without the laser hazard protector and the other line is a plot of the intensity with the pellicle laser hazard protector in place.
Figure 5:
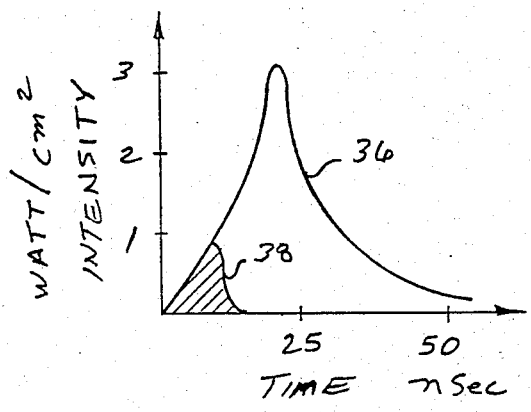
FIG. 5 is a graph of radiant intensity at the detector surface as a function of time for a short-pulse laser threat. One line is a plot of intensity without the laser hazard protector and the other line is a plot of the intensity with the pellicle.

FIGS. 4 and 5 show the intensity profiles (I) as a function of time (t) at the detector's aperture for continuous-wave (CW) and pulsed laser threats. In FIG. 4, line 32 represents the laser intensity for a continuous-wave laser source. The risetime of the intensity depends upon the slew rate of the laser beam across the sensor aperture and would therefore vary from incident to incident. The risetime and threshold of the protection system, of the laser hazard protector, are shown by line 34. The threshold is that point when the laser energy perforates the membrane and is transferred to the beam dump. The hatching underneath the curve 34 signifies the integrated energy absorbed by the detector. The absorbed energy is only a small portion of that which an unprotected system would receive.

Line 36 in FIG. 5 is a typical intensity profile for a pulsed laser. In this case, the risetime is a fundamental characteristic of the laser (for TEA $CO_2$ lasers, this risetime is on the order of 25 nanoseconds). Line 38 represents the intensity profile for a protected system, and again the hatching shows an enormous reduction in absorbed energy at the detector.

Figure 6:
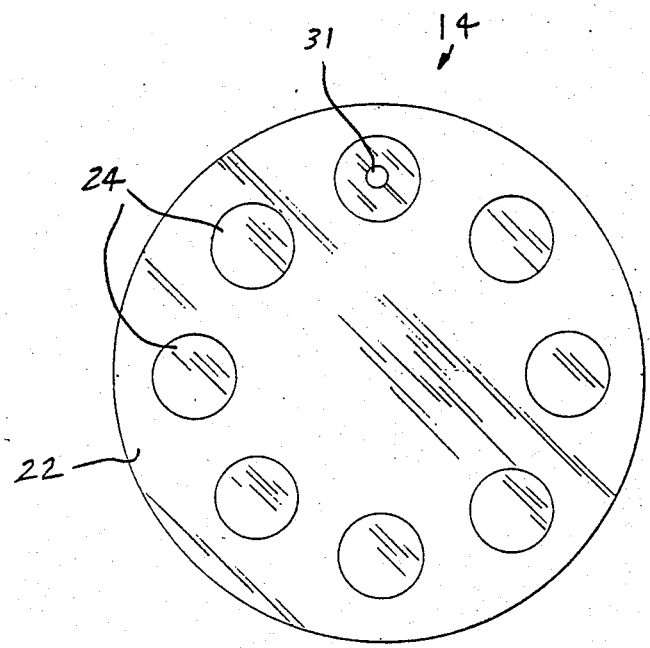
FIG. 6 is a top view of an alternative embodiment for the laser hazard protector in which a collection of small pellicle reflectors are placed in a supporting structure.

An alternative embodiment for the laser hazard protector 14 is shown in FIG. 6, where instead of one large thin-film pellicle reflector, many small pellicles 24 are placed radially around a larger support structure 22. Again, a burn hole 31 is shown within one of the reflectors. The advantage of this alternative embodiment is that there is no chance that the destruction of one of the reflector pellicles 24 would affect the performance of the others. Once all the reflectors 24 had been used up by burning separate holes in each, the entire unit would be replaced.

Although the present invention has been described in detail with respect to a particular preferred embodiment, persons possessing ordinary skill in the art to which this invention pertains will appreciate that various modifications may be made without departing from the spirit and scope of the invention.

What is claimed is:

1. Apparatus for diverting electromagnetic radiation from sensitive optical apparatus comprising:

diverting means having a reflective first part facing said electromagnetic radiation and in heat transferring relation to a second part which ablates upon heating to a given temperature, the second part being placed after said reflective first part;

means for focusing said electromagnetic radiation upon said reflective first part of said diverting means;

means for directing said reflected electromagnetic radiation towards said optical apparatus; and whereby potentially damaging electromagnetic radiation is diverted from the optical apparatus by causing the diverting meanst to change its optical characteristics when the second part ablates.

2. Apparatus for diverting electromagnetic radiation comprising:

a first thin-film reflector including a reflective layer which faces said incident electromagnetic radiation and in heat transferring relationship with a supporting layer located behind said reflective layer which ablates upon heating to a given temperature therby creating a hole in the reflector through which potentially damaging electromagnetic radiatio can pass;

focusing means which focuses said electromagnetic radiation onto said reflective layer of said reflective layer of said thin-film reflector;

means for accepting and dissipating electromagnetic energy located behind the thin film reflector;

power measuring means which detects the presence and absence of said electromagnetic energy which has passed through said thin-film reflector;

means for moving said thin-film reflector;

a feedback means which connects the signals of said power measuring means to said moving means of said thin-film reflector; and wherein an unablated portion of the first reflector or a different reflector is moved back into position to divert the electromagnetic energy when the power measuring means detects a safe level of electromagnetic energy.

3. Apparatus as claimed in claim 2 in which said thin-film reflector further comprises:

a mounting means for maintaining the optical flatness of said reflective layer; and a bonding means for joining said thin-film layers to said mounting means.

4. Apparatus as claimed in claim 3 in which is reflective layer is a thin metallic coating.

5. Apparatus as claimed in claim 3 in which said supporting layer is a thin carbon film which ablates after absorbing heat.

6. Apparatus as claimed in claim 2 in which said electromagnetic dissipation means comprises:

a thermal dissipation means for carrying away heat generated from the dissipation of electromagnetic energy; and a means for detecting the continuing presence of electromagnetic energy striking said electromagnetic dissipation means.

7. The apparatus of claim 2 which further comprises:

a plurality of said reflectors are mounted in a support structure.

8. The apparatus of claim 7 wherein said feedback means is adapted to cause said moving means to move the support until said focused electromagnetic radiation strikes a new reflector.

* * * * *